United States Patent [19]

Fiedler et al.

[11] Patent Number: 5,971,038
[45] Date of Patent: Oct. 26, 1999

[54] PROCESS AND DEVICE FOR CHECKING THE TABLET PARAMETERS

[75] Inventors: Jürgen Fiedler; Walter Hegel, both of Berlin; Hagen Bargenda; Hans Georg Körner, both of Frankfurt; Udo Wagner, Tauche; Josef Stepanek, Frankfurt, all of Germany

[73] Assignee: KORSCH Pressen GmbH, Berlin, Germany

[21] Appl. No.: 08/991,116

[22] Filed: Dec. 16, 1997

[30] Foreign Application Priority Data

Dec. 20, 1996 [DE] Germany .............................. 196 54 612

[51] Int. Cl.⁶ ....................................................... F01N 35/00
[52] U.S. Cl. ................................ 141/83; 141/94; 141/65; 141/173; 141/176; 73/78; 73/866; 33/501; 702/166
[58] Field of Search .................................. 141/83, 94, 65, 141/173, 174, 176; 7/7, 78, 821, 865, 865.8, 866; 33/501; 702/35, 155, 166

[56] References Cited

U.S. PATENT DOCUMENTS

| 4,472,960 | 9/1984 | Motoyama et al. | 73/7 |
| 4,884,463 | 12/1989 | Kay | 73/865.8 |
| 4,999,151 | 3/1991 | Hinzpeter | 265/40.4 |
| 5,439,036 | 8/1995 | Kramer | 141/1 |
| 5,515,740 | 5/1996 | Gamberini | 73/865.8 |
| 5,555,768 | 9/1996 | Shaffer et al. | 73/865.8 |
| 5,596,865 | 1/1997 | Kramer | 73/865.8 |
| 5,661,249 | 8/1997 | Rupp et al. | 73/865.8 |

FOREIGN PATENT DOCUMENTS

| 31 30 512 C2 | 2/1986 | Germany . |
| 36 28 757 A1 | 3/1988 | Germany . |
| 41 18 878 A1 | 1/1993 | Germany . |
| 43 09 978 C1 | 6/1994 | Germany . |
| 94 06 712 | 8/1994 | Germany . |

OTHER PUBLICATIONS

Korsch Pressen Gmbh, 1992, 1993 Operating Instructions for Pharmakontroll 3 NET, Korsch Pressen GmbH, Chapter 3, pp. 11, 16–18.

Korsch Pressen GmbH, 1992/1993 Operating Instructions for Pharmakontroll 3 NET, Korsch Pressen GmbH, Chapter 4, pp. 5, 9, 10, 12–16.

*Primary Examiner*—J. Casimer Jacyna
*Attorney, Agent, or Firm*—McGlew and Tuttle, P.C.

[57] ABSTRACT

A process for checking the tablet parameters weight, height and hardness by weighing and measurement, and to a device for carrying out the process as an individual device and preferably as a rotary tabletting press for permanently complying with preset tablet parameters. A process and a device for rapid, reliable, reproducible, and distortion-proof checking of optionally all parameters or selected parameters on one tablet and the overall checking of the weight on a plurality of tablets are guaranteed. This is accomplished so as to carry out individual and/or overall checks with a receiving container (1) provided for tablets (2), and the receiving container (1) is connected to stations (3, 10, 11) for the optional determination of the weight, the height, and the hardness of a single tablet (2), and from the receiving container, an individual tablet 2 and/or a plurality of tablets (2) are fed fully automatically to and removed from the individual stations (3, 10, 11) for determining the tablet weight.

11 Claims, 5 Drawing Sheets

PROCESS AND DEVICE FOR CHECKING THE TABLET PARAMETERS

FIELD OF THE INVENTION

The present invention pertains to a process for checking the tablet parameters weight, height, and hardness by weighing and measuring, preferably during the manufacture of the tablets on rotary tabletting presses, for permanently complying with preset tablet parameters, and to a device for carrying out the process as an individual device.

BACKGROUND OF THE INVENTION

Compliance with the specified tablet weight is an important quality parameter for tabletting. Any automatic control of a tabletting press is based on the relationship between the measured maximum pressing force of a tablet and the mass of the material filled into the die (tablet weight), assuming identical material data (bulk density). There is a direct relationship between the tablet weight and the pressing force needed to manufacture the tablet checked. This relationship is used for automatic monitoring and control devices on rotary presses. Depending on the material to be tabletted, a defined pressing force is associated with each tablet weight at a tablet shape preset by the compression molding dies and at a set tablet height. If the amount of the material filled in and consequently the tablet weight vary at constant tablet height, this results in a change in the pressing force in a direct dependence.

The parameters weight, height and hardness can be set more or less directly by means of specific operating parameters for every individual compression mold on modern rotary tabletting presses which have many individual compression molds on a circular path and press a large number of tablets per second.

However, the ratio of the specific operating parameters of the individual compression mold to the tablet parameter reached must be checked and regulated continuously because of the variety of the properties of the masses to be tabletted. The unambiguous assignment of the tablet parameters obtained in reality to the operating parameters of the individual compression mold must be ensured.

Devices have already been known, with which individual checks of the parameters weight, height and hardness can be performed on one tablet.

In Pharmacheck 1 (Operating Instructions for Pharmakontroll 3 NET, Chapter 3, pp. 11, 16–18, of Korsch Pressen GmbH, 1992/1993), individual tablets are sorted out from the tabletting press and are weighed in a scale. After weighing the first tablet, the scale is set to zero and a second tablet is weighed. When there are 10 or 20 tablets on the weighing scale, the scale is emptied, and the tablets are removed according to quality via three different outlet channels. Instead of the individual weighing, a batch of 10 or 20 tablets may be removed simultaneously from the tabletting press and weighed together. The weight of the individual tablets is determined by the weighings to an accuracy of 0.1 mg. The result of the weighing is used to control the degree of filling of the individual dies.

In Pharmacheck 2 (Operating Instructions for Pharmakontroll 3 NET, Chapter 4, pp. 5, 9, 10, 12–16, of Korsch Pressen GmbH, 1992/1993), individual tablets are fed to the spider rotatable around a vertical axis, and the individual tablets are fed by a rotation of the spider one after another to a weighing unit for determining the weight, to a measuring unit for determining the height or thickness, and to another measuring unit for determining the diameter and the hardness, and subsequently to an ejector unit. The process is timed at a rate of at least 6 sec per tablet and per station, so that only a small number of tablets can be checked in the case of a tabletting press having a working speed of 10,000 tablets per minute.

In addition, it is a drawback of the prior-art solutions that the performance of individual checks does not make possible a productive measurement process on a plurality of tablets, and the process cannot be carried out accurately based on individually determined tablet parameters, especially the tablet weight. As a result, the percentage of rejects is unsatisfactorily high during tabletting. It is practically impossible to resort to a certain set of data, which would make it possible, in the case of the weighing of individual tablets, to reliably recognize that the weight of the individual tablet determined corresponds to that of all the tablets produced. The parameters for height and hardness are to be determined only thereafter.

The determination of the weight, height and hardness on one tablet one after another cannot be assigned to the compression mold producing the tablet being checked with sufficient reliability, so that corrections performed on the tabletting press upon the detection of deviations often remain ineffective.

A considerable cleaning must be performed on the checking device in the case of a changeover from one type to another, because the dust-like abraded product is distributed in the entire device during the pressing and conveying of the tablets. The checking results are sometimes distorted as a result.

DE-GM 94 06 712 discloses a device for deburring and dedusting tablets with suction air, in which the tablets are conveyed by the suction of the exhaust unit over a plate chute between the tablet feed station and the tablet discharge station and are deburred and dedusted in the process. This solution is unsuitable for the subsequent checking steps on the tablets.

To carry out the height and hardness measurements, the tablets must be placed in the checking device such that tablets with approximately equal dimensions for thickness, length and diameter can also be measured in a reliable manner. The prior-art devices are unsatisfactory for this and prevent corresponding incorrect measurements only insufficiently.

SUMMARY AND OBJECTS OF THE INVENTION

The primary object of the present invention is to avoid these drawbacks and to improve the process and the device for checking the tablet parameters.

According to the invention, a process is provided for checking the tablet parameters weight, height and hardness by weighing and measurement, preferably during the manufacture of the tablets on rotary tabletting presses, for permanently complying with preset tablet parameters. An overall and/or individual checking of the tablets is optionally performed. A defined number of the tablets are introduced into a receiving container in the case of the overall check and they are conveyed onto a weighing station for the determination of their overall weight. The tablets are weighed there together with the receiving container, after which they are disposed of into a vessel. A single tablet is introduced into the receiving container in the case of the individual checking, and it is conveyed to the weighing station to determine its individual weight, and it is weighed there individually and without the receiving container. After the weighing step, it is disposed of into the vessel, or the individual tablet is moved fully automatically to and removed from the additional checking stations after the determination of the individual weight to determine its height and/or its hardness.

According to a further feature of the invention, a device is provided for carrying out the process. To carry out individual and/or overall weight checks, the receiving container for the tablets is connected to the weighing station via a conveying system. The weighing station and the checking stations for determining the height and the hardness of an individual tablet are connected to one another via a siphon arm.

A rapid, reliable, reproducible, and distortion-proof checking of optionally all parameters or of selected parameters on one tablet, and the overall checking of the weight of a plurality of tablets are guaranteed according to the invention.

Due to the sequence of checking of a combination of individual and/or overall checks in one system, the process according to the present invention and the device according to the present invention guarantee a permanent compliance with the specific tablet parameters during the manufacture, as well as a high degree of reliability of the assignment of the values measured on one tablet to the compression molds that produced that tablet.

How a sequence of individual and/or overall checks of tablets shall be performed can be defined in an event-dependent, pressing site-dependent manner or freely.

A plurality of tablets can be optionally fed to and removed from the weighing attachment fully automatically and an overall weight as well as an averaged individual weight or an individual weight of one tablet can be determined.

The process is carried out under clean conditions in the entire device due to the self-cleaning tablet conveying as well as self-cleaning of the checking assembling units.

An unambiguous orientation of all tablet geometries is ensured during the height and hardness measurement on the tablet.

Due to the modular design of the device, changes may be made with little effort at any time to adapt the device to the prevailing needs.

The replacement of assembly units, e.g., of the chute in the hardness checking station for orienting the tablets in the direction of the breaking force, is performed in a short time without tools.

The height measurement and the weighing are performed without changing elements of the device for all tablet shapes and sizes.

A substantial increase is achieved in the number of tablets that can be checked per unit of time.

The receiving container is preferably divided over its longitudinal axis and can be swung open and in the bottom area, it has slopes sloping toward the middle of the bottom and consequently toward the ejection opening. The siphon arm preferably has a suction head with a, slightly convexly curved perforated bottom, over which the tablets are held while the suction air is flowing, and wherein the suction air removes the abraded material of the tablet at the moment it is generated.

The weighing station may have a weighing attachment with a, slightly concavely downwardly bent screen insert and a weighing attachment bottom, in which the slots are arranged. A shaking means, with which the tablet is brought into the stable position corresponding to its center of gravity before the height measurement, is preferably provided in conjunction with the checking station for determining the height. A stripper for prealigning the tablets is preferably provided at the siphon arm of the internal conveying system. A chute having the cross-sectional geometry of a bent staple or with a radius between the measuring and breaking jaws may be provided, which performs the longitudinal and central alignment of the tablets of different shapes for the determination of the hardness. A scraper for cleaning the measuring and breaking jaws of the hardness-measuring station after each checking process may be provided at the chute.

The feed speed of the movable breaking jaw is preferably controllable. The calibration is dynamic and operates according to the principle of comparison, wherein a second measuring cell is introduced instead of the tablet into the calibrating device, and the calibration and the determination of the accuracy are performed by comparative measurements between the built-in measuring cell and the second measuring cell (reference measuring cell). Components for checking the weight, the height and the hardness of a said tablet are formed by independent measuring systems with separate adjustment and calibration, and that the device components for control, operation and display likewise form modules.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Referring to the drawings in particular, the invention comprises a process and device for checking tablet parameters. The device for checking the tablet parameters weight, height and hardness may be used as an individual device or in a control technical and/or mechanical connection with a tabletting press, preferably a rotary tabletting press.

The tablets, whose parameters are to be checked, are introduced from a tabletting press, not shown, into the device via a feed channel according to a preset cycle and are checked with respect to a preset test program.

The tablets may be selected from the same or different, preselectable punch stations. All or selected parameters may be checked on each individual tablet. The weight of the tablets may be determined on a number of tablets.

Figure 1:
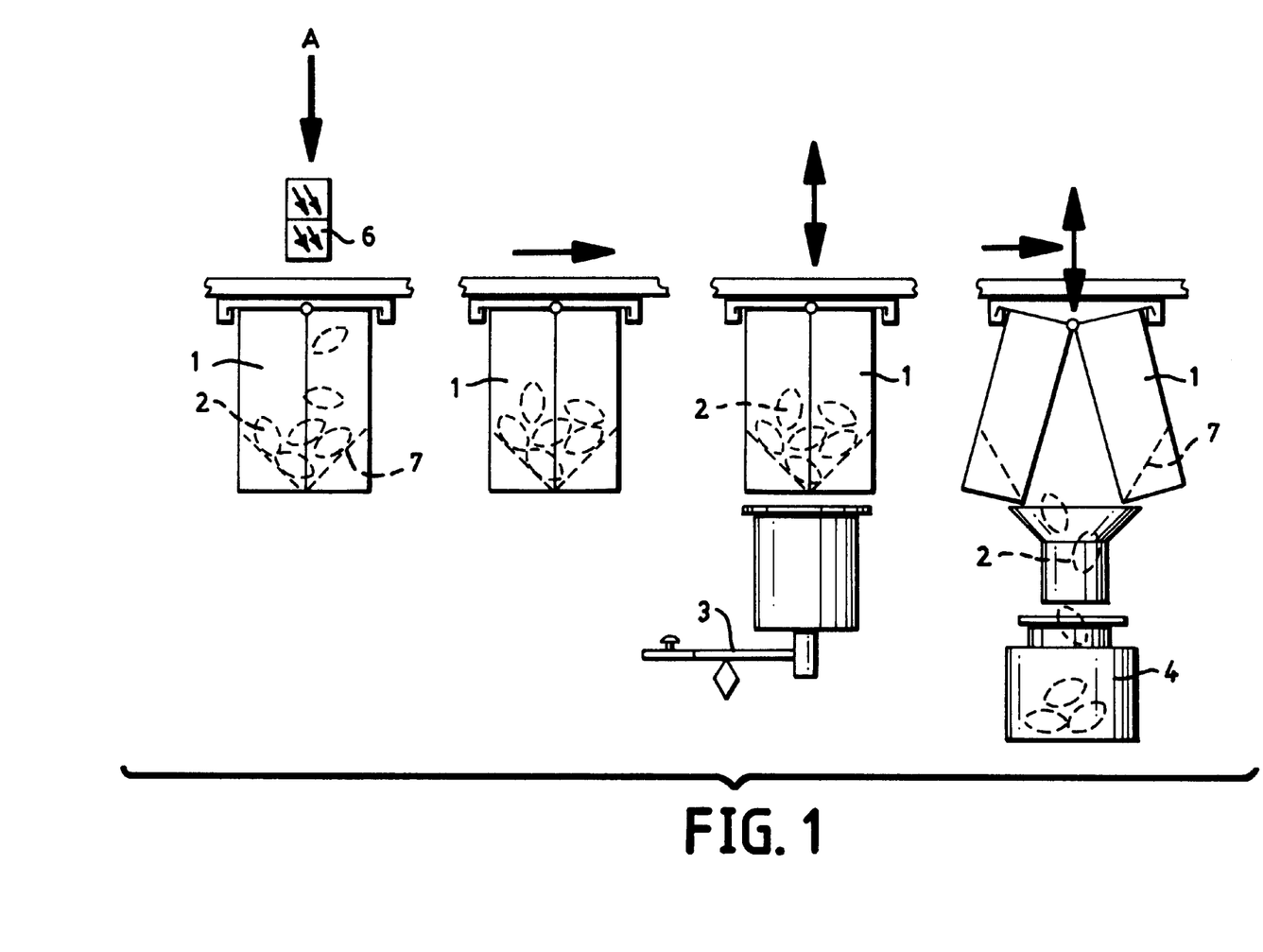
FIG. 1 is the schematic view of an overall weight-checking of tablets.

FIG. 1 shows a schematic representation of the steps in which an overall weight checking is performed on a defined number of tablets 2, e.g., 100 pieces.

A defined number of tablets 2 are filled from the outlet A of a tabletting press, not shown, into a receiving container 1 via a counting means 6, e.g., two photoelectric cells. The receiving container 1 is divided along its longitudinal axis and can be swung up, and in its lower area, it has slopes 7 sloping toward the middle of the bottom or toward the middle of the ejection opening. The receiving container 1 filled with the tablets 2 is conveyed to a weighing station 3 and is weighed together with the tablets 2 there. The measured value is evaluated in an electronic processing unit, not shown. After weighing, the receiving container 1 is moved to an emptying position, where the tablets 2 are emptied into a collecting container 4, for which purpose the receiving container 1 is swung open, and the tablets 2 slide out over the slopes 7. The receiving container 1 is then returned into its starting position and may be filled anew.

Figure 2:
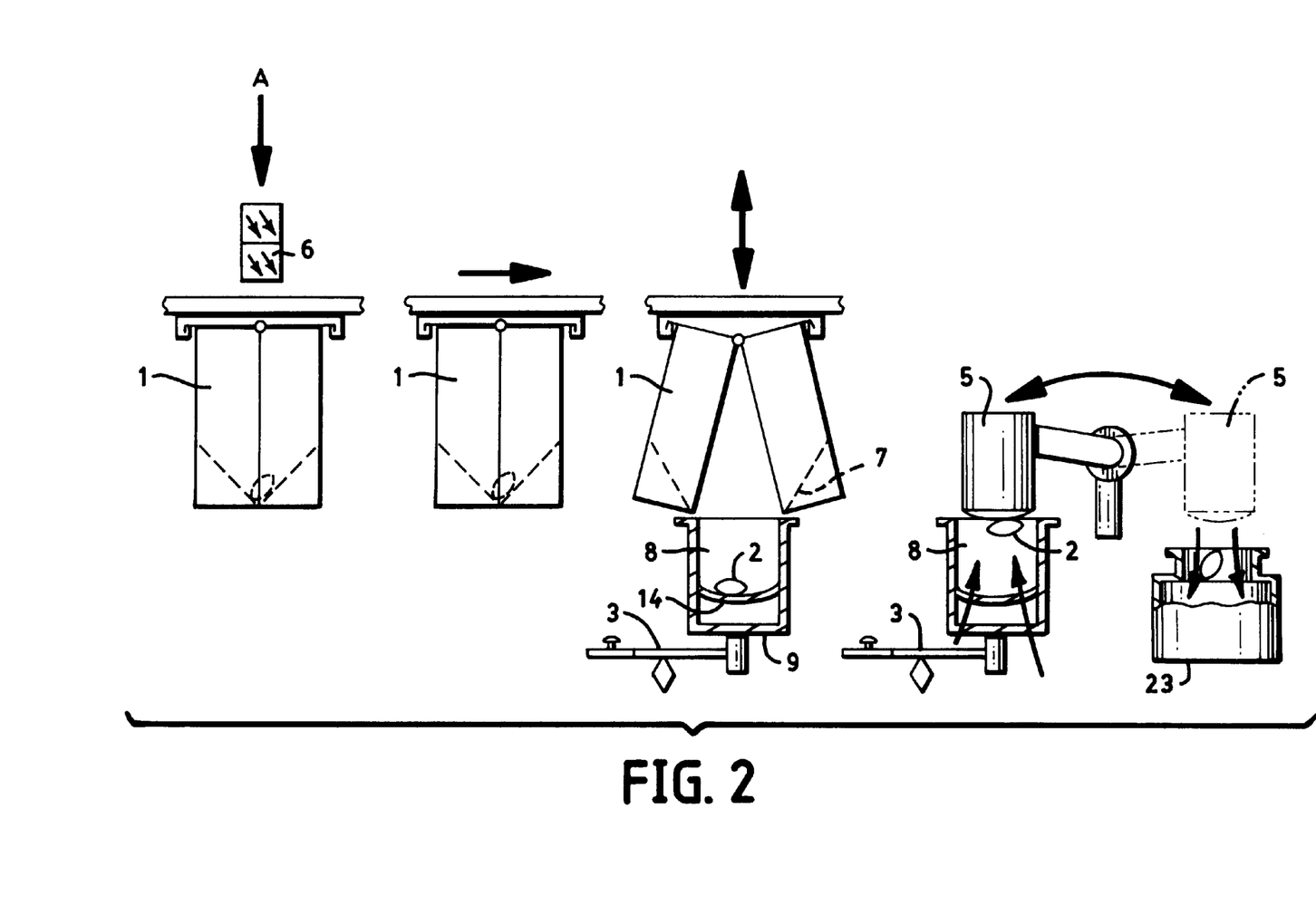
FIG. 2 is the schematic view of the individual weight-checking of tablets.

FIG. 2 shows a schematic representation of how an individual weight checking is performed with the same receiving container 1. A single tablet 2 is filled into the receiving container 1 at the outlet A of the tabletting press via the counting means 6. The receiving container 1 is moved to the weighing station 3 and is emptied there by swinging up. The tablet 2 drops onto a screen insert 14 arched concavely in the downward direction above a weighing attachment bottom 9 of a weighing attachment 8 (FIG. 3), which bottom is provided with slots 15, and it is weighed there. The weighing attachment 8 is designed such that the horizontal surfaces are minimized in order to reduce the susceptibility of the weighing to draft and in order to guarantee high accuracy at short weighing cycle time. The measured value is processed corresponding to the preset program. The individual weight checking is terminated by removing the tablet 2 from the weighing attachment 8 by means of a siphon arm 5 (FIG. 2) and moving it into the remnant container 23.

If the checking program calls for additional checks on the tablet 2 removed, the tablet 2 is conveyed to another checking station, e.g., a height-measuring station 10 (FIG. 3) or to a hardness-checking station 11 (FIGS. 4 and 5) by means of the siphon arm 5, and it is subjected to the height or hardness checking there.

Figure 3:
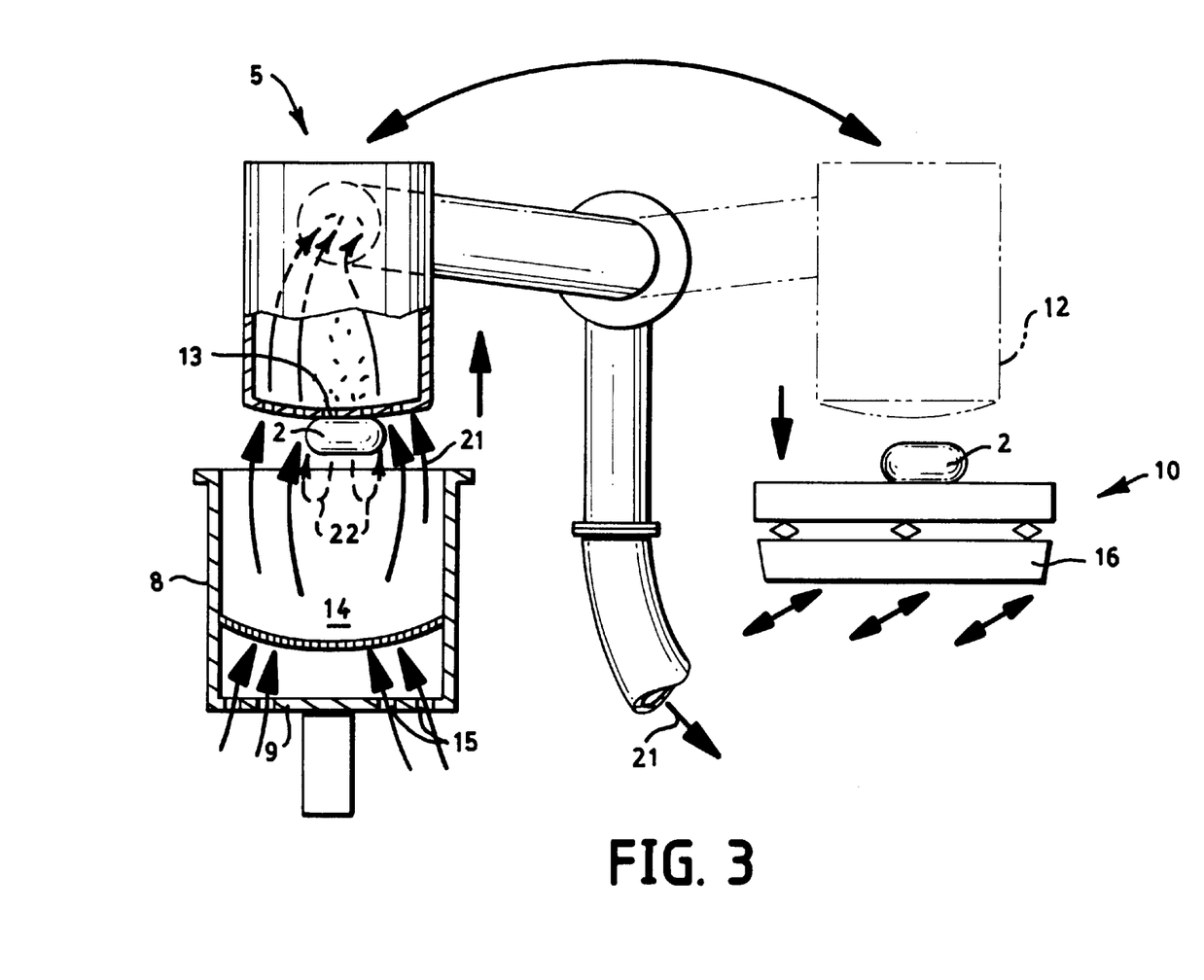
FIG. 3 is the schematic view of the tablet conveying from the weighing station to the height-checking station.

The special design of the siphon arm 5 and the special design of the weighing attachment 8 are shown schematically in FIG. 3.

The siphon arm 5 according to FIG. 3 is used for conveying the tablets between the checking stations for weighing 3, for the height or thickness checking 10, and for the hardness checking 11, and it guarantees that the measured value will be obtained under clean conditions, because no abraded material is generated, and particles present are suctioned off and are kept away from the measuring processes.

Corresponding to FIG. 3, the siphon arm 5 is formed by a suction head 12 movable via a hinge system not described in greater detail, which suction head has a convexly outwardly curved perforated bottom 13, through which air 21 is drawn via a switchable side-channel fan. The siphon arm 5 is designed such that it can be pivoted to the stations 3, 10, 11. The convexly curved perforated bottom 13 guarantees that the tablets 2 will lie in the middle of the perforated bottom 13 regardless of their shape.

To ensure the reliable function of the siphon arm 5, it is important for the weighing attachment bottom 9 of the weighing attachment 8 to have slots 15 of a defined size to ensure that a sufficient air flow 21 of a predetermined flow velocity can flow through the perforated bottom 13 of the siphon arm 5. The weighing attachment 8 contains the concavely downwardly curved screen insert 14 to bring the tablets 2 placed on it into a stable position; the tablets 2 fall over due to the curvature of the screen insert 14.

The air flow 21 guarantees the removal of all abraded parts 22 and other particles, which could distort the measurements, into a filter, not shown.

Corresponding to the representation in FIG. 3, the tablet 2 is carried by the air flow 21 and is fixed at the perforated bottom 13 of the suction head 12, and it is brought to the height-measuring station by pivoting the siphon arm 5 into a position over the checking station 10, and it is deposited there by switching off the air flow 21. A shaking means 16 under the tablet support brings the tablet 2 into the stable position corresponding to its center of gravity, so that it is guaranteed that the height or thickness of the tablet 2 will be measured according to the prior-art processes regardless of its shape. It was difficult to establish the correct position of the tablet 2 especially when the thickness measure was only slightly smaller than the second cubic measure.

Figures 4A, 4B:
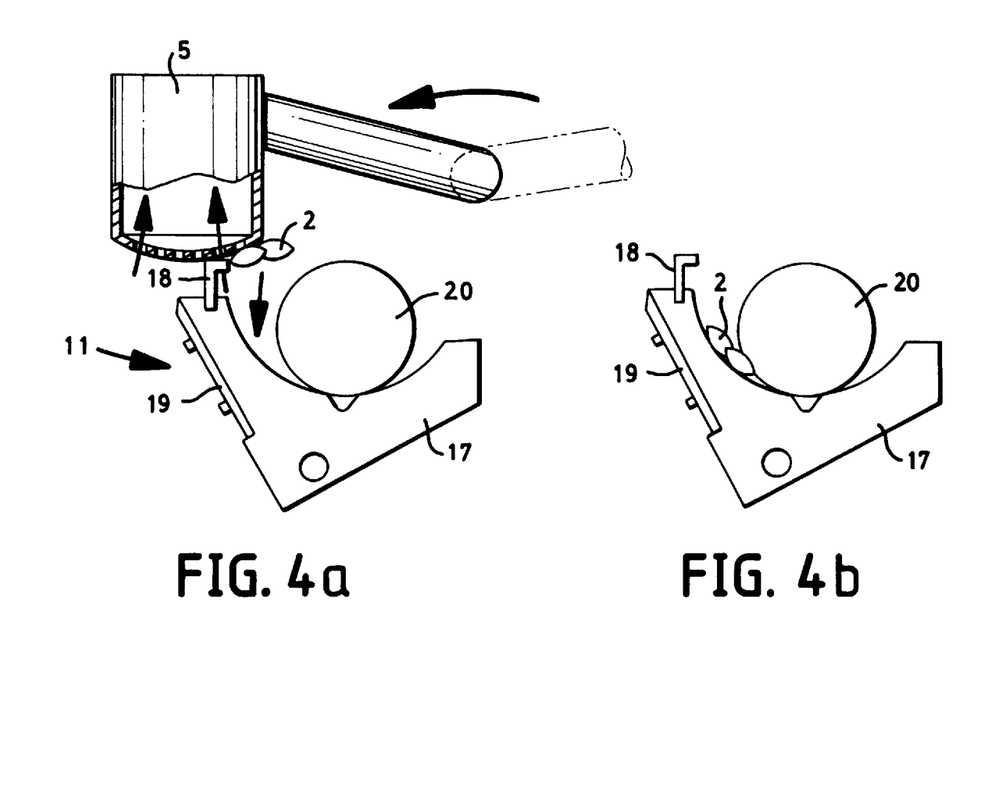
FIG. 4A is a schematic view showing the deposition of tablets using the siphon arm 5 on the checking station with a stripper.
FIG. 4B is a schematic view showing the station with tablets being brought into a prealigned position.
Figure 4C:
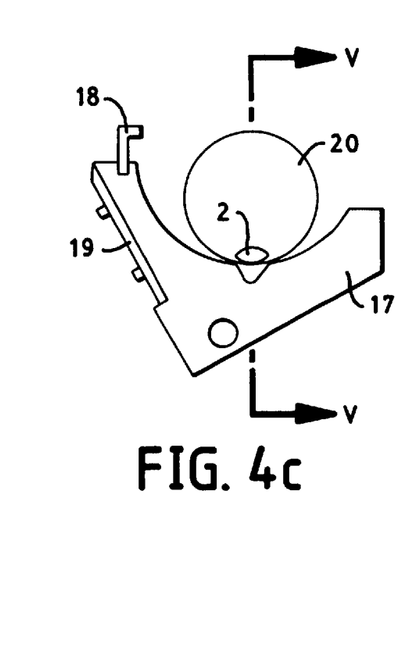
FIG. 4C is a schematic view showing a tablet sliding into a final position.

After measuring the height, the tablet 2 is conveyed by means of the siphon arm 5 to the checking station 11 for determining the hardness (FIG. 4).

Figure 5:
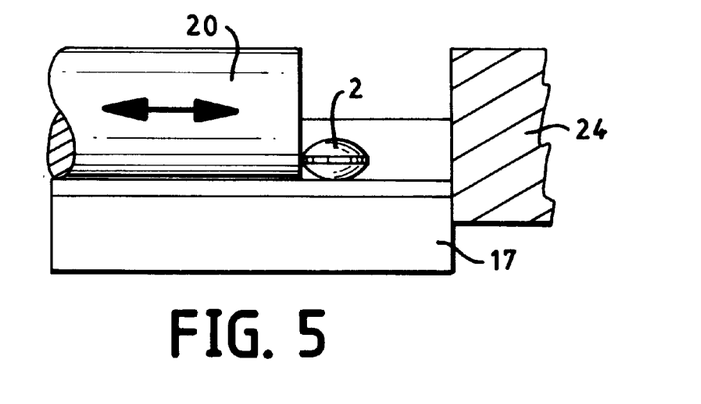
FIG. 5 is the sectional view taken along line V—V in FIG. 4C.

The measurement of the hardness of the tablet is the determination of the breaking force. The tablet is positioned between a movable breaking jaw 20 and a fixed measuring jaw 24 (FIG. 5). The movable breaking jaw 20 moves toward the fixed measuring jaw 24 until the increasing pressing force abruptly decreases. The force reached at that moment is measured as the breaking force or as the tablet hardness.

Figure 6:
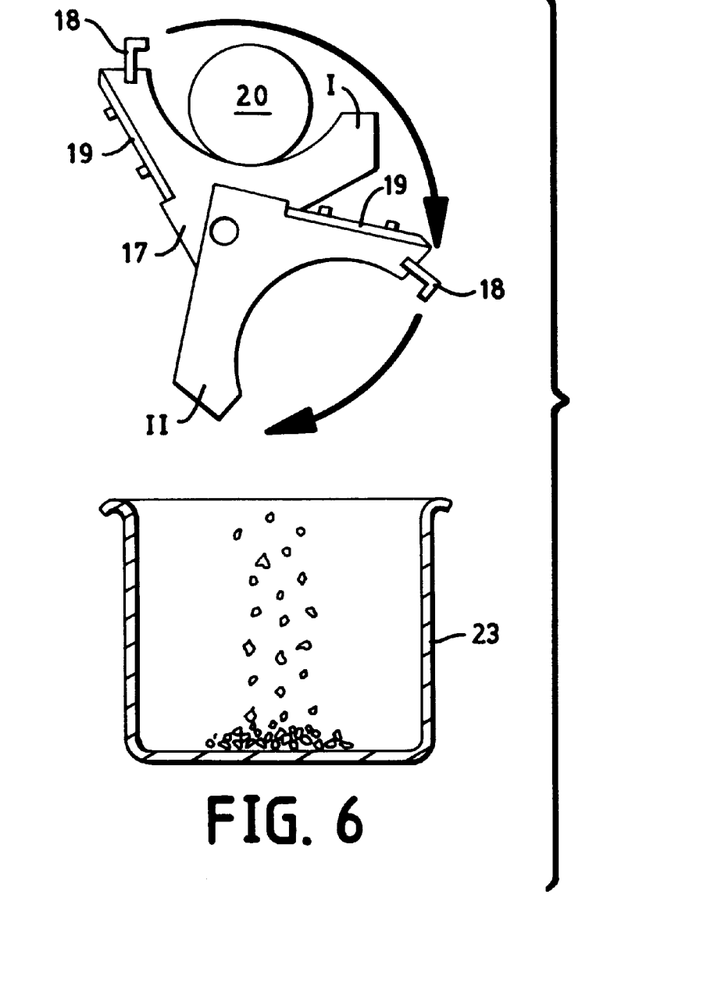
FIG. 6 is the schematic view of the scraper function.

Corresponding to the representation in FIGS. 4 through 6, the checking station 11 for checking the hardness or breaking strength has a chute 17 between the breaking jaw 20 and the measuring jaw 24, which performs, together with the feed of the jaws, the longitudinal and central alignment of the tablets 2 of different shapes with the direction of the breaking force. A stripper 18 and a scraper 19 are arranged at the chute 17.

Corresponding to the representation in FIG. 4, a prealignment of the tablets 2 is achieved by means of the stripper 18 during the deposition of the tablet 2 into the chute 17 of the checking station 11. The siphon arm S is positioned during the deposition of the tablet 2 onto the checking station 11 such (FIG. 4a) that the stripper 18 brings the tablet 2 into a prealigned position (FIG. 4b), and the tablet 2 slides into the final position (FIG. 4c) as a consequence of the geometric shape of the chute 17. The chute 17 is adapted to the geometry of the tablets 2, so that even the difficult-to-handle oblong tablets can be guided correctly and be subjected to the hardness checking. While the height and the weight are determined with one type of device elements for all tablet geometries, the chute 17 is replaced corresponding to the tablet geometry for the hardness checking.

The chute 17 preferably has a cross-sectional geometry in the form of a staple.

With the horizontal movement of the movable breaking jaw 20 (FIG. 5), the tablet 2 is pushed against a fixed part of the chute 17, which forms the fixed measuring jaw 24. The tablet 2 is aligned in the process and is ultimately destroyed. The breaking force generated in the process is measured and is subjected to further processing in the system. The breaking jaw 20 then returns into the starting position.

The function of the scraper 19 at the chute 17 is shown in FIG. 6. The measuring and breaking jaws 20 and 24 of the hardness-measuring unit, respectively, are cleaned after each checking process by means of the scraper 19. The chute 17 with the scraper 19 is moved from the resting position I into the working position II and moved along the breaking and measuring jaws 20 and 24, respectively, so that contaminants that may be present are scraped off.

To dispose of broken tablets, the chute 17 is tilted off (FIG. 6). The tablet remnants drop into a remnant container 23. The measuring and breaking jaws 20 and 24, respectively, are cleaned with the scraper 19 fastened to the chute 17 during the tilting movement to remove tablet remnants (FIG. 6). The chute 17 is then tilted into the resting position and is made ready for the next measurement.

In the prior-art devices for carrying out the hardness checking process, the feed of the movable breaking jaw is performed by means of a stepping or d.c. motor. The force applied to the tablet in this process is determined with a measuring cell. A sudden change in the increase in the force indicates that the tablet has been broken. The stepping or d.c. motor is energized with constant voltage and constant frequency. As soon as the breaking jaws touch the tablet, the tablet offers a corresponding resistance to the feed of the drive of the movable breaking jaw, depending on its hardness. The force-time characteristic resulting from this is consequently the result of the tablet hardness and of the torque of the drive still present. It is disadvantageous here that this combination of tablet hardness and the motor torque describes a curve which is valid for this individual tablet only. A reproducible measurement is therefore impossible. The dispersion of the different drives and of the energizations (even in tablet testers of the same type) lead to different curves, as a consequence of which the means and devices can be compared with one another with great tolerances only. Consequently, the feed of the movable breaking jaw is constant at idle in the state of the art.

According to the present invention, the constant feed of the movable breaking jaw 24 is replaced with a speed-controlled feed, which ensures a constant increase in force per unit in time, which increase in force can be selected in a tablet-specific manner. Instead of the exponential increase in force at the constant feed of the movable breaking jaw 24, as linear feed of the movable breaking jaw 24 with force increase is guaranteed by the application of a control. The task of this control is to maintain the increase in force per unit of time at a constant value. As a result, the resulting introduction of force into the tablet 2 will be linear at any point in time. By using the control, the variables "tablet hardness" and "motor torque" are no longer the determining values for the curve describing the force. This is the prerequisite for reproducible values. Which unit the control maintains at a constant value during the destruction of the tablet 2 is, in principle, irrelevant. The possible methods are: Constant displacement per unit of time or constant increase in force per unit of time, or constant force per unit of displacement.

Finally, the prior-art means or devices calibrate their pressure pickup or measuring jaw for the hardness tester by applying a weight after the mounting of the device. This method involves two essential drawbacks:

To perform the calibration, a conversion is performed on the measuring cell to ensure that it is not in the same mechanical position as during the checking of the tablet. The calibration is performed statically, whereas the load during the breakage of the tablet is dynamic.

These two methods are not compatible with one another, so that an error of measurement is automatically obtained due to the calibration used in the prior art.

The calibration employed in the present invention is dynamic and operates according to the principle of comparison. A second measuring cell is introduced instead of the tablet 2 between the fixed breaking jaw 24 and the movable breaking jaw 20. The calibration and the determination of the accuracy are performed by comparative measurements between the built-in measuring jaw 24 and the reference measuring cell, not shown. The calibration is performed by selecting different rates of force increase and absolute values, i.e., the entire measuring range of the device can be covered. The calibration at constant displacement takes place in a similar manner. A displacement transducer is built in instead of the measuring cell.

While a specific embodiment of the invention has been shown and described in detail to illustrate the application of the principles of the invention, it will be understood that the invention may be embodied otherwise without departing from such principles.

What is claimed is:

1. A device for checking the tablet parameters weight, height and hardness by weighing and measurement, comprising:
   a receiving container for the tablets;
   a conveying system;
   a weighing station functionally connected to said receiving container via said conveying system;
   a height checking station;
   a hardness checking station; and
   a siphon arm, said weighing station, said height checking station and said hardness checking station being functionally connected via said siphon arm.

2. The device in accordance with claim 1, wherein said receiving container is divided over its longitudinal axis and including swing open means in a bottom area, said swing open means having sloped interior surfaces sloping toward a middle of said bottom area and toward an ejection opening.

3. The device in accordance with claim 1, wherein said siphon arm has a suction air source and a suction head with a slightly convexly curved perforated bottom, over which said tablets are held while said suction air is flowing, and wherein said suction air removes abraded material of said tablet as abraded material is generated.

4. The device in accordance with claim 1, wherein said weighing station includes a weighing attachment with a slightly concavely downwardly bent screen insert and a weighing attachment bottom with slots.

5. The device in accordance with claim 1, further comprising a shaking means for bringing a tablet into a stable position corresponding to a center of gravity of the tablet, before height measurement, said shaking means being provided in conjunction with said height checking station.

6. The device in accordance with claim 1, wherein said hardness checking station includes:
   a stripper for prealigning the tablets, said striper being provided adjacent to said siphon arms and
   a chute having a cross-sectional geometry of a bent staple, which performs a longitudinal and central alignment of the tablets of different shapes for the determination of the hardness.

7. The device in accordance with claim 6, wherein a scraper is provided for cleaning measuring and breaking jaws provided with said hardness checking station after each checking process is provided at said chute.

8. The device in accordance with claim 7, wherein a feed speed of said movable breaking jaw is controllable.

9. The device in accordance with claim 6, wherein a calibration device is provided which is dynamic and operates according to the principle of comparison, wherein a second measuring cell is introduced instead of the tablet into the calibrating device, and the calibration and the determination of the accuracy are performed by comparative measurements between a built-in measuring cell and the second measuring cell acting as a reference measuring cell.

10. The device in accordance with claim 1, wherein said weighing station said height checking station and said hardness checking station include device components formed by independent measuring systems with separate adjustment and calibration, and that the device components for control, operation and display likewise form modules.

11. The device in accordance with claim 1, wherein said hardness checking station includes:

- a chute having a cross-sectional geometry with a radius which performs a longitudinal and central alignment of the tablets of different shapes for the determination of the hardness;

- a measuring jaw having a dimension greater than said chute;

- a breaking jaws having a radius smaller than said chute; and

- a stripper for prealigning the tablets, said striper being provided connected to said chute and adjacent to or at a range of motion of said siphon arm.

* * * * *